(12) United States Patent
Alman et al.

(10) Patent No.: US 9,753,041 B2
(45) Date of Patent: Sep. 5, 2017

(54) SALIVARY INFLAMMATORY BIOMARKERS ASSOCIATED WITH GLYCEMIC CONTROL AND ORAL HEALTH

(71) Applicants: Amy Christine Alman, Tampa, FL (US); Brant Roger Burkhardt, Tampa, FL (US)

(72) Inventors: Amy Christine Alman, Tampa, FL (US); Brant Roger Burkhardt, Tampa, FL (US)

(73) Assignee: UNIVERISTY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 14/692,548

(22) Filed: Apr. 21, 2015

(65) Prior Publication Data

US 2015/0301063 A1 Oct. 22, 2015

Related U.S. Application Data

(60) Provisional application No. 61/981,981, filed on Apr. 21, 2014.

(51) Int. Cl.
*G01N 33/68* (2006.01)
*G01N 33/573* (2006.01)

(52) U.S. Cl.
CPC ....... *G01N 33/6869* (2013.01); *G01N 33/573* (2013.01); *G01N 33/6863* (2013.01); *G01N 33/6866* (2013.01); *G01N 2333/96419* (2013.01); *G01N 2800/042* (2013.01); *G01N 2800/18* (2013.01)

(58) Field of Classification Search
None
See application file for complete search history.

(56) References Cited

U.S. PATENT DOCUMENTS

2008/0171396 A1* 7/2008 Fung ...................... G01N 33/66
436/86

OTHER PUBLICATIONS

Costa et al. Salivary interleukin-6, matrix metalloproteinase-8, and osteoprotegerin in patients with periodontitis and diabetes. J Periodontol. Mar. 2010;81(3):384-91.*
Cytokines, in MeSH Database, National Center for Biotechnology Information, Bethesda, Maryland, USA [online], [retrieved on Jan. 27, 2016]. Retrieved from the Internet: <URL: http://www.ncbi.nlm.nih.gov/mesh/68016207>.*
Jackson et al. Update of human and mouse matrix metalloproteinase families. Hum Genomics. Feb. 2010;4(3):194-201.*
Kakade et al. Periodontal status of type I diabetics compared to non-diabetic participants: a preliminary study. Ceylon Med J. Mar. 2014;59(1):19-20.*
Caseiro et al. Salivary proteome and peptidome profiling in type 1 diabetes mellitus using a quantitative approach. J Proteome Res. Apr. 5, 2013;12(4):1700-9. Epub Feb. 25, 2013.*
Huang RP. Cytokine protein arrays. Methods Mol Biol. 2004;264:215-31.*
Demmer RT, Papapanou PN., Epidemiologic patterns of chronic and aggressive periodontitis. Periodontol 2000 2010;53:28-44.
Cobb CM, Williams KB, Gerkovitch MM., Is the prevalence of periodontitis in the USA in decline? Periodontol 2000 2009;50:13-24.
Offenbacher S, Beck JD, Moss K, Results From the Periodontitis and Vascular Events (PAVE) Study: A Pilot Multicentered, Randomized, Controlled Trial to Study Effects of Periodontal Therapy in a Secondary Prevention Model of Cardiovascular Disease. J Periodontol 2009;80:190-201.
Noble JM, Borrell LN, Papapanou PN, Elkind MS, Scarmeas N, Wright CB. Periodontitis is associated with cognitive impairment among older adults: analysis of NHANES-III. J Neurol Neurosurg Psychiatry 2009;80:1206-11.
Mealey BL, Rose LF. Diabetes mellitus and inflammatory periodontal diseases. Curr Opin Endocrinol Diabetes Obes 2008;15:135-41.
Mealey BL, Oates TW. Diabetes mellitus and periodontal diseases. J Periodontol 2006;77:1289-303.
Lalla E, Cheng B, Lal S., Periodontal changes in children and adolescents with diabetes: a casecontrol study. Diabetes Care 2006;29:295-9.
Mealey BL,. Periodontal disease and diabetes. A two-way street. J Am Dent Assoc 2006;137 Suppl:26S-31S.
Campus G, Salem A, Uzzau S, Baldoni E, Tonolo G., Diabetes and periodontal disease: a case-control study. J Periodontol 2005;76:418-25.
Tsai C, Hayes C, Taylor GW., Glycemic control of type 2 diabetes and severe periodontal disease in the US adult population. Community Dent Oral Epidemiol 2002;30:182-92.
Liese AD, Lawson A, Song HR., Evaluating geographic variation in Type 1 and type 2 diabetes mellitus incidence in youth in four US regions. Health Place 2010;16:547-56.
Atkinson MA, Maclaren NK., The pathogenesis of insulin-dependent diabetes mellitus. N Engl J Med 1994;331:1428-36.
Mealey B., Diabetes and periodontal diseases. J Periodontol 1999;70:935-49.
Nathan DM, Lachin J, Cleary P., Intensive diabetes therapy and carotid intima-media thickness in Type 1 diabetes mellitus. N Engl J Med 2003;348:2294-303.
Kilpatrick ES, Keevil BG, Jagger C, Spooner RJ, Small M., Determinants of raised C-reactive protein concentration in Type 1 diabetes. QJM 2000;93:231-6.
King DE, Mainous AG, 3rd, Buchanan TA, Pearson WS., C-reactive protein and glycemic control in adults with diabetes. Diabetes Care 2003;26:1535-9.
Schram MT, Chaturvedi N, Schalkwijk CG, Fuller JH, Stehouwer CD, Group EPCS. Markers of inflammation are cross-sectionally associated with microvascular complications and cardiovascular disease in Type 1 diabetes—the EURODIAB Prospective Complications Study. Diabetologia 2005;48:370-8.

(Continued)

*Primary Examiner* — David Romeo
(74) *Attorney, Agent, or Firm* — Saliwanchik, Lloyd & Eisenschenk

(57) ABSTRACT

The present invention provides non-invasive diagnostic methods and kits for determining and/or monitoring oral health and glycemic control in subjects with Type 1 diabetes.

3 Claims, No Drawings

(56) References Cited

OTHER PUBLICATIONS

Chiappin S, Antonelli G, Gatti R, De Palo EF., Saliva specimen: a new laboratory tool for diagnostic and basic investigation. Clin Chim Acta 2007;383:30-40.
Lima DP, Diniz DG, Moimaz SA, Sumida DH, Okamoto AC., Saliva: reflection of the body. Int J Infect Dis 2010;14:e184-8.
Giannobile WV, Beikler T, Kinney JS, Ramseier CA, Morelli T, Wong DT., Saliva as a diagnostic tool for periodontal disease: current state and future directions. Periodontol 2000 2009;50:52-64.
Gursoy UK, Könönen E, Uitto V-J., Salivary interleukin-1βconcentration and the presence of multiple pathogens in periodontitis. J Clin Periodontol 2009;36:922-7.
Gursoy UK, Kononen E, Pradhan-Palikhe P., Salivary MMP-8, TIMP-1, and ICTP as markers of advanced periodontitis. J Clin Periodontol 2010;37:487-93.
Eke PI, Thornton-Evans GO, Wei L, Borgnakke WS, Dye BA. Accuracy of NHANES periodontal examination protocols. J Dent Res 2010;89:1208-13.
Darveau RP. Periodontitis: a polymicrobial disruption of host homeostasis. Nat Rev Microbiol 2010;8:481-90.
Garlet GP. Destructive and protective roles of cytokines in periodontitis: a re-appraisal from host defense and tissue destruction viewpoints. J Dent Res 2010;89:1349-63.
Smit MD, Westra J, Vissink A, Doornbos-Van Der Meer B, Brouwer E, Van Winkelhoff AJ., Periodontitis in established rheumatoid arthritis patients: a cross-sectional clinical, microbiological and serological study. Arthritis Res Ther 2012;14:R222.
Dietrich T, Sharma P, Walter C, Weston P, Beck J., The epidemiological evidence behind the association between periodontitis and incident atherosclerotic cardiovascular disease. J Periodontol 2013;84:S70-84.
Kim HD, Sim SJ, Moon JY, Hong YC, Han DH., Association between periodontitis and hemorrhagic stroke among Koreans: a case-control study. J Periodontol 2010;81:658-65.
Mealey BL, Ocampo GL., Diabetes mellitus and periodontal disease. Periodontol 2000 2007;44:127-53.
Atkinson MA, Eisenbarth GS., Type 1 diabetes: new perspectives on disease pathogenesis and treatment. Lancet 2001;358:221-9.
Imperatore G, Boyle JP, Thompson TJ., Projections of Type 1 and type 2 diabetes burden in the U.S. population aged <20 years through 2050: dynamic modeling of incidence, mortality, and population growth. Diabetes Care 2012;35:2515-20.
Miller LS, Manwell MA, Newbold D., The relationship between reduction in periodontal inflammation and diabetes control: a report of 9 cases. J Periodontol 1992;63:843-8.
Grossi SG, Skrepcinski FB, Decaro T, Zambon JJ, Cummins D, Genco RJ., Response to periodontal therapy in diabetics and smokers. J Periodontol 1996;67:1094-102.
Grossi SG, Skrepcinski FB, Decaro T., Treatment of periodontal disease in diabetics reduces glycated hemoglobin. J Periodontol 1997;68:713-9.
Kiran M, Arpak N, Unsal E, Erdogan MF., The effect of improved periodontal health on metabolic control in type 2 diabetes mellitus. J Clin Periodontol 2005;32:266-72.
Papapanou PN, Sedaghatfar MH, Demmer RT., Periodontal therapy alters gene expression of peripheral blood monocytes. J Clin Periodontol 2007;34:736-47.
Ziegler R, Heidtmann B, Hilgard D, Hofer S, Rosenbauer J, Holl R., Frequency of SMBG correlates with HbA1c and acute complications in children and adolescents with Type 1 diabetes. Pediatr Diabetes 2011;12:11-7.
Franciosi M, Pellegrini F, De Berardis G., The impact of blood glucose self-monitoring on metabolic control and quality of life in type 2 diabetic patients: an urgent need for better educational strategies. Diabetes Care 2001;24:1870-7.
Franciosi M, Pellegrini F, De Berardis G., Self-monitoring of blood glucose in non-insulin-treated diabetic patients: a longitudinal evaluation of its impact on metabolic control. Diabet Med 2005;22:900-6.
Rosilio M, Cotton JB, Wieliczko MC., Factors associated with glycemic control. A cross-sectional nationwide study in 2,579 French children with Type 1 diabetes. The French Pediatric Diabetes Group. Diabetes Care 1998;21:1146-53.
Simmons JH, McFann KK, Brown AC., Reliability of the Diabetes Fear of Injecting and Self-Testing Questionnaire in pediatric patients with Type 1 diabetes. Diabetes Care 2007;30:987-8.
Hamilton JG., Needle phobia: a neglected diagnosis. J Fam Pract 1995;41:169-75.
Edgar WM., Saliva: its secretion, composition and functions. Br Dent J 1992;172:305-12.
Lyu SY, Morisky DE, Yeh CY, Twu SJ, Peng EY, Malow RM., Acceptability of rapid oral fluid HIV testing among male injection drug users in Taiwan, 1997 and 2007. AIDS Care 2011;23:508-14.
White B, Day C, Thein HH., Acceptability of hepatitis C virus testing methods among injecting drug users. Drug Alcohol Rev 2008;27:666-70.
Pfaffe T, Cooper-White J, Beyerlein P, Kostner K, Punyadeera C., Diagnostic potential of saliva: current state and future applications. Clin Chem 2011;57:675-87.
Dillon MC, Opris DC, Kopanczyk R., Detection of homocysteine and C-reactive protein in the saliva of healthy adults: comparison with blood levels. Biomark Insights 2010;5:57-61.
Hu S, Arellano M, Boontheung P., Salivary proteomics for oral cancer biomarker discovery. Clin Cancer Res 2008;14:6246-52.
Streckfus C, Bigler L, Dellinger T, Dai X, Kingman A, Thigpen JT., The presence of soluble c-erbB-2 in saliva and serum among women with breast carcinoma: a preliminary study. Clin Cancer Res 2000;6:2363-70.
Caseiro A, Ferreira R, Padrao A., Salivary Proteome and Peptidome Profiling in Type 1 Diabetes Mellitus Using a Quantitative Approach. J Proteome Res 2013 [epub ahead of print].
Cabras T, Pisano E, Mastinu A., Alterations of the salivary secretory peptidome profile in children affected by Type 1 diabetes. Mol Cell Proteomics 2010;9:2099-108.
Caseiro A, Vitorino R, Barros AS., Salivary peptidome in Type 1 diabetes mellitus. Biomed Chromatogr 2012;26:571-82.
Loesche WJ, Syed SA, Stoll J., Trypsin-like activity in subgingival plaque. A diagnostic marker for spirochetes and periodontal disease? J Periodontol 1987;58:266-73.
Ramseier CA, Kinney JS, Herr AE., Identification of pathogen and host-response markers correlated with periodontal disease. J Periodontol 2009;80:436-46.
Giannobile WV., Salivary diagnostics for periodontal diseases. J Am Dent Assoc 2012;143:6S-11S.
Gilbert GH, Litaker MS., Validity of self-reported periodontal status in the Florida dental care study. J Periodontol 2007;78:1429-38.
Rabinovitch A., Immunoregulatory and cytokine imbalances in the pathogenesis of IDDM. Therapeutic intervention by immunostimulation? Diabetes 1994;43:613-21.
Rabinovitch A, Suarez-Pinzon W, El-Sheikh A, Sorensen O, Power RF. Cytokine gene expression in pancreatic islet-infiltrating leukocytes of BB rats: expression of Th1 cytokines correlates with beta-cell destructive insulitis and IDDM. Diabetes 1996;45:749-54.
Green EA, Eynon EE, Flavell RA., Local expression of TNFalpha in neonatal NOD mice promotes diabetes by enhancing presentation of islet antigens. Immunity 1998;9:733-43.
Ebersole JL, Schuster JL, Stevens J., Patterns of salivary analytes provide diagnostic capacity for distinguishing chronic adult periodontitis from health. J Clin Immunol 2013;33:271-9.
Standards of Medical Care in Diabetes—2012. Diabetes Care 2012;35 Suppl 1:S11-63.
Hannas AR, Pereira JC, Granjeiro JM, Tjaderhane L., The role of matrix metalloproteinases in the oral environment. Acta Odontol Scand 2007;65:1-13.
Silva JA, Ferrucci DL, Peroni LA., Sequential IL-23 and IL-17 and increased Mmp8 and Mmp14 expression characterize the progression of an experimental model of periodontal disease in Type 1 diabetes. J Cell Physiol 2012;227:2441-50.
Alman AC, Kinney GL, Tracy RP., Prospective Association Between Inflammatory Markers and Progression of Coronary Artery Calcification in Adults With and Without Type 1 Diabetes. Diabetes Care 2013., [epub ahead of print].

(56) References Cited

OTHER PUBLICATIONS

Tofighi D, Mackinnon DP., RMediation: An R package for mediation analysis confidence intervals. Behavior Research Methods 2011;43:692-700.

Behle JH, Sedaghatfar MH, Demmer RT., Heterogeneity of systemic inflammatory responses to periodontal therapy. J Clin Periodontol 2009;36:287-94.

Preshaw PM, Alba AL, Herrera D, Jepsen S, Konstantinidis A, Makrilakis K, et al., Periodontitis and diabetes: a two-way relationship. Diabetologia. 2012;55(1):21-31.

Atkinson MA, Eisenbarth GS, Michels AW., Type 1 diabetes. Lancet. 2014;383(9911):69-82.

Ajita M, Karan P, Vivek G, S Ma, Anuj M., Periodontal disease and Type 1 diabetes mellitus: associations with glycemic control and complications: an Indian perspective. Diabetes Metab Syndr. 2013;7(2):61-3.

Yoon AJ, Cheng B, Philipone E, Turner R, Lamster IB., Inflammatory biomarkers in saliva: assessing the strength of association of diabetes mellitus and periodontal disease with the oral inflammatory burden. J Clin Periodontol. 2012;39(5):434-40.

Kaufman E, Lamster IB., The diagnostic applications of saliva—A review. Crit Rev Oral Biol M. 2002;13(2):197-212.

Caseiro A, Ferreira R, Padrao A, Quintaneiro C, Pereira A, Marinheiro R, et al., Salivary Proteome and Peptidome Profiling in Type 1 Diabetes Mellitus Using a Quantitative Approach. J Proteome Res. 2013;12(4):1700-9.

Gursoy UK, Kononen E, Pussinen PJ, Tervahartiala T, Hyvarinen K, Suominen AL, et al., Use of host- and bacteria-derived salivary markers in detection of periodontitis: A cumulative approach. Dis Markers. 2011;30(6):299-305.

Rathnayake N, Akerman S, Klinge B, Lundegren N, Jansson H, Tryselius Y, et al., Salivary biomarkers for detection of systemic diseases. PLoS One. 2013;8(4):e61356.

Miller CS, King CP, Jr., Langub MC, Kryscio RJ, Thomas MV., Salivary biomarkers of existing periodontal disease: a cross-sectional study. J Am Dent Assoc. 2006;137(3):322-9.

Binnie V, McHugh S, MacPherson L, Borland B, Moir K, Malik K., The validation of self-reported smoking status by analysing cotinine levels in stimulated and unstimulated saliva, serum and urine. Oral Dis. 2004;10(5):287-93.

Etter JF, Vu Duc T, Perneger TV., Saliva cotinine levels in smokers and nonsmokers. Am J Epidemiol. 2000;151(3):251-8.

Dakovic D, Colic M, Cakic S, Mileusnic I, Hajdukovic Z, Stamatovic N., Salivary interleukin-8 levels in children suffering from Type 1 diabetes mellitus. J Clin Pediatr Dent. 2013;37(4):377-80.

Engebretson SP, Hey-Hadavi J, Ehrhardt FJ, Hsu D, Celenti RS, Grbic JT, et al., Gingival crevicular fluid levels of interleukin-1beta and glycemic control in patients with chronic periodontitis and type 2 diabetes. J Periodontol. 2004;75(9):1203-8.

Engebretson SP, Vossughi F, Hey-Hadavi J, Emingil G, Grbic JT., The influence of diabetes on gingival crevicular fluid beta-glucuronidase and interleukin-8. J Clin Periodontol. 2006;33(11):784-90.

Engebretson SP, Hyman LG, Michalowicz BS, Schoenfeld ER, Gelato MC, Hou W, et al., The effect of nonsurgical periodontal therapy on hemoglobin A1c levels in persons with type 2 diabetes and chronic periodontitis: a randomized clinical trial. JAMA. 2013;310(23):2523-32.

Bencharit S, Baxter SS, Carlson J, Byrd WC, Mayo MV, Border MB, et al., Salivary proteins associated with hyperglycemia in diabetes: a proteomic analysis. Mol Biosyst. 2013;9(11):2785-97.

Wang XX, Han X, Guo XJ, Luo XL, Wang DL., The Effect of Periodontal Treatment on Hemoglobin A1c Levels of Diabetic Patients: A Systematic Review and Meta-Analysis. Plos One. 2014;9(9).

Teeuw WJ, Gerdes Vea, Loos BG., Effect of Periodontal Treatment on Glycemic Control of Diabetic Patients—A systematic review and meta-analysis. Diabetes care. 2010;33(2):421-7.

Sgolastra F, Severino M, Pietropaoli D, Gatto R, Monaco A., Effectiveness of Periodontal Treatment to Improve Metabolic Control in Patients With Chronic Periodontitis and Type 2 Diabetes: A Meta-Analysis of Randomized Clinical Trials. J Periodontol. 2013:84(7):958-73.

Engebretson S, Kocher T., Evidence that periodontal treatment improves diabetes outcomes: a systematic review and meta-analysis. J Clin Periodontol. 2013;40:S153-S63.

Miller CS, Foley JD, Bailey AL, Campell CL, Humphries RL, Christodoulides N, et al., Current developments in salivary diagnostics. Biomark Med. 2010;4(1):171-89.

Gursoy UK, Kononen E, Huumonen S, Tervahartiala T, Pussinen PJ, Suominen AL, et al., Salivary type I collagen degradation end-products and related matrix metalloproteinases in periodontitis. Journal of Clinical Periodontology. 2013;40(1):18-25.

\* cited by examiner

SALIVARY INFLAMMATORY BIOMARKERS ASSOCIATED WITH GLYCEMIC CONTROL AND ORAL HEALTH

CROSS-REFERENCE TO RELATED APPLICATION

This application claims the benefit of U.S. Provisional Application Ser. No. 61/981,981, filed Apr. 21, 2014, which is hereby incorporated by reference in its entirety.

BACKGROUND

Periodontitis impacts as much as 47% of the U.S. population and is a significant cause for tooth loss in adults (Eke et al., 2010). Periodontitis is a chronic inflammatory lesion of the supporting structures of the teeth and is one of the most widely distributed and prevalent human diseases (Demmer et al., 2010; Cobb et al., 2009); this destructive process is driven by bacterial infections that colonize the tooth root surface (Darveau, 2010). Studies have demonstrated bacteremia and increased systemic inflammation appear to contribute to several diseases, such as cardiovascular disease, Alzheimer's disease, and diabetes (Offenbacher et al., 2009; Noble et al., 2009; Mealey et al., 2008). Studies have shown that there is a strong, bi-directional, relationship between diabetes and periodontal disease in which glycemic control is a major determinant (Mealey et al., 2008; Mealey et al., 2006; Lalla et al., 2006; Mealey et al., 2006; Campus et al., 2005; Tsai et al., 2002). However, additional pathways independent of glycemic control may exist that contribute to enhanced periodontal destruction in those with diabetes (Mealey et al., 2006). Type 1 diabetes (T1D) is an autoimmune disease resulting in the targeted destruction of pancreatic beta-cells and permanent loss of insulin production and is a leading cause of chronic disease in youth and young adults (Liese et al., 2010). Hyperglycemia is a classic manifestation of the disease (Atkinson et al., 1994; Mealey, 1999) and is a risk factor for complications such as atherosclerosis (Nathan et al., 2003). Hence, glycemic control is essential for disease management. Hemoglobin A1c (HbA1c), a measure of glycemic control, has been associated with increased levels of systemic inflammation (Kilpatrick et al, 2000; King et al., 2003), with concordant association with vascular complications of diabetes (Schram et al., 2005).

Saliva is an emerging and promising biofluid that has many advantages over serum, particularly the ease of collection and of storage (Chiappin et al., 2007; Lima et al., 2010). Most previous studies of biomarkers in diabetes have examined serum, however, serum is difficult and costly to obtain, and its large proteomic dynamic range has made novel biomarker analysis and subsequent interpretation confusing. Measurement of salivary biomarkers has been demonstrated in some populations, particularly for investigating periodontal disease (Giannobile et al., 2009; Gursoy et al., 2009; Gursoy et al., 2010), but little has been published on their presence in the saliva of Type 1 diabetics and their association with glycemic control.

BRIEF SUMMARY

The present invention provides non-invasive diagnostic methods and kits for determining and/or monitoring oral health, glycemic control, and/or diabetes progression in subjects with Type 1 diabetes.

In one aspect, a method of monitoring/determining glycemic control, diabetes progression, and/or oral health in a subject with Type 1 diabetes comprises:
  obtaining a saliva sample from the subject;
  determining a level of one or more cytokine and/or matrix metalloproteinase (MMP) in the saliva sample; and
  comparing the level of the one or more cytokine and/or MMP in the saliva sample to a reference value;
  wherein an elevated level of the one or more cytokine and/or MMP in the saliva sample compared to the reference value indicates that the subject has decreased glycemic control, decreased oral health, and/or diabetic progression.

In another aspect, a kit for monitoring oral health, diabetic progression, and/or glycemic control comprises:
  an application zone for receiving a saliva sample;
  a labeling zone containing a binding agent that binds to at least one of a cytokine and/or MMP in the sample; and
  a detection zone where a cytokine- and/or MMP-bound binding agent is retained to give a signal, wherein the signal given for a sample of a subject with the cytokine/MMP level greater than a control level is different from the signal given for a sample of a subject with the cytokine/MMP level lower than a control level.

In some embodiments, the cytokine being measured in the methods and kits provided herein is selected from the group consisting of IL-1β, IL-6, IL-8, IL-10, TNF-α, and IFN-γ. Likewise, the MMP being measured is selected from the group consisting of MMP-1, MMP2, MMP-3, MMP-7, MMP-8, MMP-9 and MMP-10.

In additional aspects, the present invention provides methods of improving glycemic control (i.e., stabilizing blood sugar levels), treating diabetes progression, and/or improving oral health/treating oral inflammation in a subject with Type 1 diabetes.

DETAILED DISCLOSURE

Periodontitis is driven by bacterial infections that colonize the tooth root surface (Darveau, 2010). Due to this pathogenic event, immunological mediators are activated and various metabolic byproducts such as cytokines, chemokines and tissue-destructive enzymes such as matrix-metalloproteinases (MMPs) are released (Garlet, 2010). Spillover of these immunological mediators into the general circulation is thought to play a role in the development and exacerbation of systemic diseases, particularly poorly controlled diabetes, whereby a bi-directional relationship between periodontal disease and glycemic control has been suggested (Mealey, 2006; Preshaw et al., 2012). Type 1 diabetes (T1D) is a highly complex polygenic autoimmune disease resulting in the loss of pancreatic β-cells and absence of insulin production (Atkinson et al., 2014). While the relationship between periodontal disease and glycemic control has been demonstrated in T1D (Ajita et al., 2013), the association between oral immunological mediators and glycemic control in T1D is not well understood and has not been precisely measured. The overall suspected relationship between periodontal disease and glycemic control provides a strong rationale for the hypothesis that increased inflammatory burden and quantitative biomarkers of periodontal disease are associated with decreased glycemic control.

Saliva is a clear mucoserous exocrine derived liquid containing a mixture of secretions from the submandibular, parotid, sublingual and minor glands that provides a representation of overall health status and oral inflammatory burden (Edgar, 1992; Pfaffe et al., 2011; Yoon et al., 2012). Saliva can be obtained noninvasively, safely and economically with minimal processing and required training by personnel. Inflammatory molecules within the saliva are derived from the periodontium via influx of gingival crevicular fluid (GCF) and from the mucosa (Kaufman, 2002). This bio-collection serves as a highly accessible and useful general measurement of oral inflammatory and periodontal burden. Despite the tremendous potential and utility of the saliva for the examination of biomarkers related to systemic disease, limited studies have been conducted in understanding and evaluating the salivary inflammatory burden specifically in T1D (Caseiro et al., 2013; Cabras et al., 2010; Caseiro et al., 2012). At present, numerous potential surrogate measures of existing periodontal disease and oral health have been identified and include cytokines and MMPs such as interleukin-1β (IL-1β), tumor necrosis factor (TNF)-α, and matrix metalloproteinase (MMP)-8 (Yoon et al., 2012; Gursoy et al., 2011; Rathnayake et al., 2013; Miller et al., 2006). The utility of these biomarkers has been demonstrated in terms of association with decreased oral health but there are currently no published reports that have examined the association between oral inflammation and levels of HbA1c within T1D.

The present invention addresses the aforementioned issues and provides non-invasive diagnostic methods and kits for determining and/or monitoring oral health (e.g., salivary inflammatory burden), Hemoglobin A1c ($HbA_{1c}$), which is a measure of glycemic control, and/or diabetes progression in subjects with Type 1 diabetes. The present invention defines panels of salivary inflammatory, pathogen, and proteome biomarkers in Type 1 diabetics and identifies pathways associated with both glycemic control and periodontal status. Distinct and overlapping salivary biomarker profiles encompassing inflammatory, pathogen, and proteome pathways distinguish subjects on the basis of glycemic control and oral health. Further, these profiles are able to enhance clinical treatment and management. Also, increased salivary inflammatory burden via cytokine detection is associated with decreased glycemic control and oral health. The pairing of defined analytes with statistical analysis establishes parameters to discriminate health from disease. In addition, the present invention serves as a foundation for innovative development of other screening tools utilizing saliva for rapid and economical diabetes disease management.

The present invention can be used to examine the association between salivary inflammatory burden with glycemic control ($HbA_{1c}$) and self-reported gingival condition in adult T1D subjects.

The term "subject," as used herein, describes an organism, including mammals such as primates. Mammalian species that can benefit from the subject methods include, but are not limited to, apes, chimpanzees, orangutans, humans, monkeys; and domesticated and/or laboratory animals such as dogs, cats, horses, cattle, pigs, sheep, goats, chickens, mice, rats, guinea pigs, and hamsters. Typically, the subject is a human.

In one aspect, the method of monitoring/determining glycemic control, diabetes progression, and/or oral health in a subject with Type 1 diabetes comprises:

obtaining a saliva sample from the subject;

determining a level of one or more cytokine and/or matrix metalloproteinase (MMP) in the saliva sample; and comparing the level of the one or more cytokine and/or MMP in the saliva sample to a reference value;

wherein an elevated level of the one or more cytokine and/or MMP in the saliva sample compared to the reference value indicates that the subject has decreased glycemic control, decreased oral health, and/or diabetic progression.

In some embodiments, the cytokine being measured in the methods and kits provided herein is selected from the group consisting of IL-1β, IL-6, IL-8, IL-10, TNF-α, and IFN-γ. Likewise, the MMP being measured is selected from the group consisting of MMP-1, MMP2, MMP-3, MMP-7, MMP-8, MMP-9 and MMP-10. In preferred embodiments, the cytokine being measured in the methods and kits provided herein is TNF-α. In a further preferred embodiment, the MMP being measured is selected from MMP-8, MMP-9, or a combination thereof.

Determination of levels or concentrations of cytokine and/or MMP in the saliva sample can be made at protein or nucleic acid (e.g., mRNA) levels. Such determination can be made using conventional methods, including but not limited to, enzyme-linked immunosorbant assay (ELISA), Western blot, immunoprecipitation, immunofluorescence, radioimmunoassay, immunocytochemistry, polymerase chain reaction (PCR) methods including reverse transcription polymerase chain reaction (RT-PCR), enzyme-linked immunosorbent spot (ELISpot) assay, Northern blot, nucleic acid hybridization techniques, fluorescent polarization (FO) technology, nucleic acid amplification techniques, transcription mediated amplification (TMA), DNA strand displacement amplification (SDA), multiplexed bead immunoassay or a combination thereof.

The level of cytokine and/or MMP in the saliva sample can be determined based on protein level. In one embodiment, the level of cytokine and/or MMP can be determined by contacting an antibody, aptamer, or binding partner that specifically binds to the specific cytokine and/or MMP molecule being analyzed (such as IFN-γ). An antibody that specifically recognizes, or specifically binds to, a specific cytokine and/or MMP (such as IFN-γ) can be in any of a variety of forms, including intact immunoglobulin molecules, fragments of immunoglobulin molecules such as Fv, Fab and similar fragments; multimers of immunoglobulin molecules (e.g., diabodies, triabodies, and bi-specific and tri-specific antibodies, as are known in the art); fusion constructs containing an antibody or antibody fragment; and human or humanized immunoglobulin molecules or fragments thereof.

Antibodies within the scope of the invention can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

Antibodies useful according to the present invention include polyclonal and monoclonal antibodies. The term "monoclonal antibody," as used herein, refers to an antibody or antibody fragment obtained from a substantially homogeneous population of antibodies or antibody fragments (i.e. the individual antibodies within the population are identical except for possible naturally occurring mutations that may be present in a small subset of the antibody molecules).

In one embodiment, the level of cytokine and/or MMP (such as IFN-γ) is determined by contacting the saliva sample with one or more antibody that specifically recognizes, or specifically binds to, the cytokine and/or MMP (such as IFN-γ); and detecting the complex formed between the antibody and the cytokine and/or MMP (such as IFN-γ).

The level of a cytokine and/or MMP (such as IFN-γ) can be determined based on mRNA level of the specific cytokine or MMP being measured. In one embodiment, the mRNA level of a cytokine or MMP can be determined by a method comprising contacting the saliva sample with a polynucleotide probe that comprises a nucleic acid sequence that specifically binds to, or hybridizes under stringent conditions with, the mRNA of the specific cytokine or MMP molecule being measured; and detecting the complex formed between the polynucleotide probe and the mRNA of the cytokine or MMP.

In one embodiment, the mRNA level of the cytokine and/or MMP can be determined by polymerase chain reaction methods. Polymerase chain reaction (PCR) is a process for amplifying one or more target nucleic acid sequences present in a nucleic acid sample using primers and agents for polymerization and then detecting the amplified sequence. The extension product of one primer when hybridized to the other becomes a template for the production of the desired specific nucleic acid sequence, and vice versa, and the process is repeated as often as is necessary to produce the desired amount of the sequence.

The reference value can be readily established by skilled healthcare practitioners. The reference value can be established, for example, by measuring the cytokine or MMP level(s) of interest in control saliva samples obtained from subjects who do not have Type 1 diabetes, or alternatively have good oral health. Usually, the reference value is the cut-off value that distinguishes patients with Type 1 diabetes from subjects without Type 1 diabetes. The presence or elevation of the level of the cytokine and/or MMP being measured in a subject's sample, as compared to the reference value, is diagnostic of Type 1 diabetes (or poor glycemic control). Preferably, the control subjects do not have Type 1 diabetes, inflammation, poor oral health, or decreased glycemic control. Further, the reference value is preferably provided by using the same type of biological sample and the same assay technique as is used for measurement of the subject's level (e.g., IFN-γ level), to avoid any error in standardization.

The reference value can also be established by determining an initial level from the cytokine or MMP level(s) of interest in a saliva sample obtained from a subject who is to be monitored over time. As such, the reference value may be an initial level from the subject (before or after Type 1 diabetes onset), which is determined to be a baseline. Alternatively, the reference value can be determined from a reference population or subject with Type 1 diabetes and/or with confirmed clinical characteristics that are being measured by the methods herein.

In another aspect, methods of improving glycemic control (i.e., stabilizing blood sugar levels), treating diabetes progression, and/or improving oral health/treating oral inflammation in a subject with Type 1 diabetes comprises:

obtaining a saliva sample from the subject;

determining a level of one or more cytokine and/or matrix metalloproteinase (MMP) in the saliva sample;

comparing the level of the one or more cytokine and/or MMP in the saliva sample to a reference value, wherein an elevated level of the one or more cytokine and/or MMP in the saliva sample compared to the reference value indicates that the subject has decreased glycemic control, decreased oral health/inflammation, and/or diabetic progression; and administering a pharmaceutically acceptable, effective amount of an agent, drug or pharmaceutical composition if the subject has decreased glycemic control, decreased oral health, oral inflammation, and/or diabetic progression. The administering of an agent, drug or pharmaceutical composition provides improved glycemic control (typical levels of blood sugar (glucose), improved oral health, decreased oral inflammation, and/or halts or reverses diabetic progression or symptoms thereof.

As used herein, "treating" or "improving" refers to arresting or inhibiting, or attempting to arrest or inhibit, the development or progression of a disease and/or causing, or attempting to cause, the reduction, suppression, regression, or remission of a disease and/or a symptom thereof. As would be understood by those skilled in the art, various clinical and scientific methodologies and assays may be used to assess the development or progression of a disease, and similarly, various clinical and scientific methodologies and assays may be used to assess the reduction, regression, or remission of a disease or its symptoms. "Treatment" refers to both therapeutic treatment and prophylactic or preventative measures. Those in need of treatment include those already with the disease as well as those prone to have the disease or those in whom the disease is to be prevented.

The terms "effective amount" and "therapeutically effective amount," used interchangeably, as applied to the an agent, drug or pharmaceutical compositions described herein, mean the quantity necessary to render the desired therapeutic result. For example, an effective amount is a level effective to treat, cure, or alleviate the symptoms of diabetes for which the agent, drug or pharmaceutical composition is being administered. Amounts effective for the particular therapeutic goal sought will depend upon a variety of factors including the disorder being treated and its severity and/or stage of development/progression; the bioavailability and activity of the specific agent, drug or pharmaceutical composition used; the route or method of administration and introduction site on the subject; the rate of clearance of the specific agent, drug or pharmaceutical composition and other pharmacokinetic properties; the duration of treatment; inoculation regimen; drugs used in combination or coincident with the specific agent, drug or pharmaceutical composition; the age, body weight, sex, diet, physiology and general health of the subject being treated; and like factors well known to one of skill in the relevant scientific art. Some variation in dosage will necessarily occur depending upon the condition of the subject being treated, and the physician or other individual administering treatment will, in any event, determine the appropriate dosage for an individual patient.

The term "pharmaceutically acceptable," as used herein with regard to pharmaceutical compositions, means approved by a regulatory agency of the Federal or a state government or listed in the U.S. Pharmacopeia or other generally recognized pharmacopeia for use in animals and/or in humans.

The agents, drugs, and/or pharmaceutical compositions may include any therapeutic agents, as would be understood by those skilled in the art, that would treat the underlying symptoms and/or causes of Type 1 diabetes, glycemic irregularities, and/or decreased oral health. Examples of agents/drugs useful for such treatments can include insulin, antibiotics, etc. Agents/drugs can also be administered in combination or as a single pharmaceutical composition/formulation, as would be understood by the skilled artisan.

In another aspect, a kit for monitoring oral health, diabetic progression, and/or glycemic control comprises:

an application zone for receiving a saliva sample;

a labeling zone containing a binding agent that binds to at least one of a cytokine and/or MMP in the sample; and a detection zone where a cytokine- and/or MMP-bound binding agent is retained to give a signal, wherein the signal given for a sample of a subject with the cytokine/MMP level greater than a control level is different from the signal given for a sample of a subject with the cytokine/MMP level lower than a control level.

In certain specific embodiments, the kit comprises an application zone for receiving a biological sample (such as a saliva sample); a labeling zone containing a binding agent that binds to a specific cytokine or MMP (e.g., IFN-γ) or correpsonding mRNA in the sample; and a detection zone where a specific cytokine or MMP (e.g., IFN-γ)-bound binding agent is retained to give a signal, wherein the signal given for a sample of a subject with the level of the cytokine or MMP (e.g., IFN-γ) greater than a control level is different from the signal given for a sample of a subject with the level of the same cytokine or MMP (e.g., IFN-γ) lower than a control level.

In one embodiment, the kit comprises a polynucleotide probe that comprises a nucleic acid sequence that specifically binds to, or hybridizes under highly stringent conditions, an mRNA of a cytokine or MMP (e.g., IFN-γ) of interest; and a primer set that amplifies the mRNA of a cytokine or MMP (e.g., IFN-γ) of interest.

Optionally, the kit may include any material useful for performing the present diagnostic method as described above. For instance, the kit may further comprise agents that are useful for detection or visualization of antigen-induced immune responses (e.g., IFN-γ responses) in saliva samples. Such agents include antibodies that recognize IFN-γ or reporter molecules that provide identifiable signals for analysis of IFN-γ levels. In addition, the kit may further comprise agents that preserve or maintain peptide antigen molecules.

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions.

The methods of the invention can be carried out using a diagnostic kit for qualitatively or quantitatively detecting a cytokine or MMP in saliva. By way of example, the kit can contain binding agents (e.g., antibodies) specific for the cytokine or MMP of interest, antibodies against the antibodies labeled with an enzyme; and a substrate for the enzyme. The kit can also contain a solid support such as microtiter multi-well plates, standards, assay diluent, wash buffer, adhesive plate covers, and/or instructions for carrying out a method of the invention using the kit. In one embodiment, the kit includes one or more protease inhibitors (e.g., a protease inhibitor cocktail) to be applied to the biological sample to be assayed (such as saliva).

The agent(s) can be packaged with a container for collecting the saliva sample from a patient. When the antibodies or binding partner are used in the kits in the form of conjugates in which a label is attached, such as a radioactive metal ion or a moiety, the components of such conjugates can be supplied either in fully conjugated form, in the form of intermediates or as separate moieties to be conjugated by the user of the kit.

Thus, the following non-limiting embodiments are provided:

1. A method of monitoring glycemic control in a subject with Type 1 diabetes, comprising:
  obtaining a saliva sample from the subject;
  determining a level of one or more cytokine and/or matrix metalloproteinase (MMP) in the saliva sample; and
  comparing the level of the one or more cytokine and/or MMP in the saliva sample to a reference value;
  wherein an elevated level of the one or more cytokine and/or MMP in the saliva sample compared to the reference value indicates that the subject has decreased glycemic control.

2. The method according to embodiment 1, wherein the cytokine is selected from IL-1β, IL-6, IL-8, IL-10, TNF-α, and IFN-γ.

3. The method according to embodiment 1, wherein the cytokine is TNF-α.

4. The method according to embodiment 1, wherein the MMP is selected from MMP-1, MMP2, MMP-3, MMP-7, MMP-8, MMP-9, and MMP-10.

5. The method according to embodiment 1, wherein the MMP is selected from MMP-8, MMP-9, or a combination thereof.

6. The method according to embodiment 1, wherein the level of cytokine and/or MMP in the saliva sample is determined using enzyme-linked immunosorbant assay (ELISA), Western blot, immunoprecipitation, immunofluorescence, radioimmunoassay, immunocytochemistry, reverse transcription polymerase chain reaction (RT-PCR), enzyme-linked immunosorbent spot (ELISpot) assay, Northern blot, nucleic acid hybridization technique, fluorescent polarization (FO) technology, nucleic acid amplification technique, transcription mediated amplification (TMA), DNA strand displacement amplification (SDA), multiplexed bead immunoassay or a combination thereof.

7. The method according to embodiment 1, wherein the level of cytokine and/or MMP in the saliva sample is determined by contacting the saliva sample with an antibody, aptamer, or binding partner that specifically binds to the specific cytokine and/or MMP being measured.

8. A method of monitoring oral health in a subject with Type 1 diabetes, comprising:
  obtaining a saliva sample from the subject;
  determining a level of one or more cytokine and/or matrix metalloproteinase (MMP) in the saliva sample; and
  d) comparing the level of the one or more cytokine and/or MMP in the saliva sample to a reference value;
  wherein an elevated level of the one or more cytokine and/or MMP in the saliva sample compared to the reference value indicates that the subject has decreased oral health.

9. The method according to embodiment 8, wherein the cytokine is selected from IL-1β, IL-6, IL-8, IL-10, TNF-α, and IFN-γ.

10. The method according to embodiment 8, wherein the cytokine is TNF-α.

11. The method according to embodiment 8, wherein the MMP is selected from MMP-1, MMP2, MMP-3, MMP-7, MMP-8, MMP-9 and MMP-10.

12. The method according to embodiment 8, wherein the MMP is selected from MMP-8, MMP-9, or a combination thereof.

13. The method according to embodiment 8, wherein the level of cytokine and/or MMP in the saliva sample is determined using enzyme-linked immunosorbant assay (ELISA), Western blot, immunoprecipitation, immunofluorescence, radioimmunoassay, immunocytochemistry, reverse transcription polymerase chain reaction (RT-PCR), enzyme-linked immunosorbent spot (ELISpot) assay, Northern blot, nucleic acid hybridization technique, fluorescent polarization (FO) technology, nucleic acid amplification technique, transcription mediated amplification (TMA), DNA strand displacement amplification (SDA), multiplexed bead immunoassay or a combination thereof.

14. The method according to embodiment 8, wherein the level of cytokine and/or MMP in the saliva sample is determined by contacting the saliva sample with an antibody, aptamer, or binding partner that specifically binds to the specific cytokine and/or MMP being measured.

15. A kit for monitoring oral health and/or glycemic control, the kit comprising:
   an application zone for receiving a saliva sample;
   a labeling zone containing a binding agent that binds to at least one of a cytokine and/or MMP in the sample; and
   a detection zone where a cytokine- and/or MMP-bound binding agent is retained to give a signal, wherein the signal given for a sample of a subject with the cytokine/MMP level greater than a control level is different from the signal given for a sample of a subject with the cytokine/MMP level lower than a control level.

16. The kit according to embodiment 15, wherein the cytokine is selected from IL-1β, IL-6, IL-8, IL-10, TNF-α, and IFN-γ.

17. The kit according to embodiment 15, wherein the cytokine is TNF-α.

18. The kit according to embodiment 15, wherein the MMP is selected from MMP-1, MMP2, MMP-3, MMP-7, MMP-8, MMP-9, and MMP-10.

19. The kit according to embodiment 15, wherein the MMP is selected from MMP-8, MMP-9, or a combination thereof.

EXAMPLES

Following are examples that illustrate procedures for practicing the invention. These examples should not be construed as limiting. It will be appreciated that variations in proportions and alternatives in elements of the components shown will be apparent to those skilled in the art and are within the scope of embodiments of the present invention. Theoretical aspects are presented with the understanding that Applicants do not seek to be bound by the theory presented. All percentages are by weight and all solvent mixture proportions are by volume unless otherwise noted.

In order to facilitate the understanding of the following examples, certain frequently occurring materials and methods will be described.

Participants—

A cross-sectional observation study of 150 T1D patients consecutively recruited from the Diabetes Center at the University of South Florida, aged 18 or older, was conducted to examine the association between salivary inflammation and glycemic control. Subjects were recruited during regularly scheduled clinic visits. Of the 150 that were enrolled and that provided an unstimulated whole saliva sample (described below), 6 subjects were excluded from this analysis due to their saliva being very viscous and/or evidently contaminated with blood. Nine additional subjects were excluded from the MMP analysis due to inadequate quantity of saliva. Only 2 subjects approached refused to participate in the study on the basis of overall apprehension of salivary collection. Since there are no published reports of the relationship between HbA1C and salivary cytokine levels in T1D, we have had to base sample size calculations on data from an independent cohort study of adult T1D that used serum measurements. The independent cohort we used did not have measurements for all of the inflammatory cytokines that we measure, and due to the possibility that individual inflammatory markers may act on several different pathways to arrive at the same outcome, we based the sample size calculation on a measure of inflammatory burden. We would have a power of >80% to detect a difference in sample means of 0.29 in the inflammatory burden variable using a dichotomization of subjects on HbA1C of ≥mean vs. <mean. The study was reviewed and approved by the University of South Florida Institutional Review Board. All participants provided informed written consent prior to participation in the study.

Clinical Data Collection—

All enrolled patients in the study completed the oral health questionnaire. This questionnaire consisted of two questions regarding gingival condition: 1) Compared to others your age, how would you rate the current condition of your gums: poor, fair, good, excellent, and 2) Do you have a loose tooth? These questions were previously shown to be correlated with clinically determined periodontal health (Gilbert and Litaker, 2007). Additional information obtained from the patient chart at the time of the clinic visit included body mass index (BMI), duration of diabetes, age, sex, race, and glycated hemoglobin (HbA1c), a measure of glycemic control.

Saliva Collection—

Each participant passively drooled in a 2 mL collection tube with an attached salivary collection aid (Saliva Biol LLC No. 61/524,096 patent). Approximately 1 to 1.5 ml of saliva was collected from each subject. Immediately upon collection a protease and phosphatase inhibitor cocktail (EDTA-free Thermo Scientific Halt, Thermos Fisher Scientific, Rockford, Ill., USA) was added at 1× to inhibit proteolysis. The sample was centrifuged for 5 minutes at 5500 rpm in a refrigerated centrifuge set at −10° C. The saliva sample was then distributed into 100 μL aliquots and stored immediately at −80° C. until multiplexing analysis. Commercially received saliva (Innovative Research, Novi, Mich., USA) was also aliquoted and stored frozen to be later used within each multiplexing batch for the purpose of quality control.

Cytokine Analysis—

Cytokine levels were determined using a multiplexed bead immunoassay and measured with a Luminex MAGPIX instrument (Luminex, Austin, Tex., USA). Six cytokines: IL-1β, IL-6, IL-8, IL-10, TNF-α, and IFN-γ was measured using the high sensitivity human cytokine magnetic bead assay (EMD Millipore, Cat No. HSCYTMAG-60SK-06, Billerica, Mass., USA) following manufacturer instructions. Each assay was analyzed on the Luminex MAGPIX instrument to measure inflammatory concentrations followed by a 5-parameter logistic curve-fitting method from a standard curve of each respective analyte. Saliva samples were normalized by equivalent volume (155 μL) and examined in duplicate per each assay run. The high sensitivity human cytokine magnetic bead kit provides a minimum detectable concentration of IL-1β (0.06 pg/mL), IL-6 (0.20 pg/mL), IL-8 (0.05 pg/mL), IL-10 (0.48 pg/mL), TNF-α (0.07 pg/mL), and IFN-γ (0.18 pg/mL). Quality control samples of non-T1D saliva were included in each assay run to account for any potential intra or inter-assay variability to ensure that % CV did not exceed 3%. Concentration was calculated by the StatLIA® Immunoassay Analysis software (Brendan Technologies), by measuring the true limits of detection for an assay by mathematically determining what the empirical Minimum Detectable Concentration (MinDC) would be if an infinite number of standard concentrations were run for the assay under the same conditions. Measurements were performed in triplicate.

MMP Analysis—

Human matrix metalloproteinase (MMP) levels were determined using a multiplexed bead immunoassay. Three MMPs: MMP-3, MMP-8, and MMP-9 were measured using the high sensitivity human MMP Base magnetic bead assay (R&D systems Inc, Catalog number LMPM000, Minneapolis, Minn., USA). The plate was analyzed on the Luminex MAGPIX® instrument as described above for determination of cytokine concentration. Measurements were performed in triplicate.

Cotinine Analysis—

Salivary cotinine levels were measured utilizing a commercial ELISA (Salimetrics, Catalog Number 1-2002, Carlsbad, Calif., USA) according to manufacturer's instructions. Cotinine levels (ng/ml) were determined from 20 μl of saliva and measured in duplicate. Due to saliva volume limitations, cotinine levels were determined for 95 of the 144 subjects. Results are reported as means and standard deviations.

Statistical Analysis—

Data are presented as means and standard deviations for continuous variables and as the number of subjects and percent for categorical data. Distributions of all of the cytokines and MMPs were found to be skewed and were log transformed for all analyses. For these variables, the data are presented as the geometric mean and interquartile range. All cytokines were adequately measured within the linear range of the generated standard curve with the exception of IFN-γ which was only measured in 2.1% of all salivary samples analyzed and therefore excluded from further analyses. Cotinine-derived smoking status was determined using a cutoff value of 15 ng/ml (Binnie et al., 2004; Etter et al., 2000).

Principal components analysis (PCA) with orthogonal rotation was used to produce linear components of the cytokine and MMP variables with shared variance. PCA is a variable reduction technique used to account for redundancy between variables by producing uncorrelated components that account for a meaningful amount of the variance contained in the original set of variables but that can be used simultaneously in a regression analysis. Components may be thought of as independent constructs represented by the markers that load highly on that component. Interpretability of the final solution was a major determinant of the minimum number of components to be used in the analyses. Individual cytokines were considered to load highly on a given component with factor loads >0.6. Factor loads indicate the correlation of individual markers on each component. Multiple linear (HbA1c) and logistic (gingival condition) regression analyses were performed to examine the relationships between the PCA components and HbA1c and gingival condition. Both the linear (HbA1c) and logistic (gingival condition) models were adjusted for age, sex, duration of diabetes, and BMI. The HbA1c model was additionally adjusted for gingival condition and the gingival condition model was additionally adjusted for HbA1c. Cotinine-derived smoking status, race, and time of saliva collection were evaluated as potential confounders and not found to alter the parameter estimates for the PCA components in either model by more than 10%, so these were not retained in the final models. All data analyses were performed using SAS/STAT 9.3 software (SAS Institute Inc., Cary, N.C.).

Example 1

Study Design and Concentrations of Cytokines and MMPs in Saliva

The overall characteristics of the subject population are shown in Table 1. The mean age of subjects in this study population was 35.8 (±16.5) years. The study population had slightly more females than males (59% vs 41%) and was predominantly white (79.2%). The mean duration of diabetes was 18.4 (±12.9) years, with a mean $HbA_{1c}$ of 8.3 (±1.7), and a mean BMI of 27.4 (±6.3). Cotinine values indicated that 18 (19.0%) were current smokers. The geometric means of the analytes ranged from 0.25 pg/ml for TNF-α to 305.0 ng/ml for MMP-9.

TABLE 1

| Subject characteristics (n = 144) | |
|---|---|
| Age (years)* | 35.8 ± 16.5 |
| Male (n)† | 59 (41.0) |
| Race/ethnicity (n)† | |
| White | 114 (79.2) |
| Black | 13 (9.0) |
| Hispanic | 12 (8.3) |
| Other | 5 (3.5) |
| Duration of diabetes (years)* | 18.4 ± 12.9 |
| HbA1c (%)* | 8.3 ± 1.7 |
| BMI (kg/m²)* | 27.4 ± 6.3 |
| BMI category (n)† | |
| Underweight (<18.5 kg/m²) | 5 (3.5) |
| Normal (18.5-<25 kg/m²) | 52 (36.1) |
| Overweight (25-<30 kg/m²) | 51 (35.4) |
| Obese (≥30 kg/m²) | 36 (25.0) |
| Cotinine (ng/ml)‡,§ | 1.1 (0.3-1.7) |
| Current smoker (n; cotinine > 15 ng/ml)†,§ | 18 (19.0) |
| Time of day of saliva collection (n)* | |
| Morning (8:50 am to 11:58 am) | 54 (37.5) |
| Afternoon (12:00 pm to 5:07 pm) | 90 (62.5) |
| Condition of gums (n)† | |
| Excellent | 20 (13.9) |
| Very Good | 43 (30.0) |
| Good | 53 (36.8) |
| Fair | 25 (17.4) |
| Poor | 3 (2.1) |
| Has a loose tooth (n)† | 5 (3.5) |
| IL-6 (pg/ml)‡ | 1.8 (0.61-6.8) |
| IL-8 (pg/ml)‡ | 54.6 (22.2-118.3) |
| IL-10 (pg/ml)‡ | 6.9 (2.6-18.6) |
| IL-1β (pg/ml)‡ | 1.1 (0.27-4.7) |
| TNF-α (pg/ml)‡ | 0.25 (0.13-0.50) |
| MMP-3 (pg/ml)‡,‖ | 197.5 (77.3-377.0) |
| MMP-8 (ng/ml)‡,‖ | 84.1 (35.5-183.6) |
| MMP-9 (ng/ml)‡,‖ | 305.0 (140.4-680.7) |

*Data presented as mean ± SD
†Data presented as number (%)
‡Data presented as geometric mean (25th-75th percentile)
§N = 95
‖N = 135

Example 2

Principal Components Analysis

Table 2 presents the 5-component solution derived from the PCA. MMP-8 and MMP-9 were positively correlated with component 1 with factor loads of 0.89 and 0.88, respectively. IL-6, IL-1β, and IL-8 (factor loads of 0.82, 0.70, and 0.63, respectively) were highly correlated with component 2. Components 3, 4, and 5 were correlated with single analytes, TNF-α (factor load of 0.84), IL-10 (factor load of 0.87), and MMP-3 (factor load of 0.79), respectively. Subjects with high values on any or all of these components would also have high values for the respective markers that loaded highly on the component.

TABLE 2

Principal components analysis with orthogonal rotation of the individual cytokines and MMPs

| Component 1 | | Component 2 | | Component 3 | | Component 4 | | Component 5 | |
|---|---|---|---|---|---|---|---|---|---|
| Marker | Load* | Marker | Load* | Marker | Load* | Marker | Load* | Marker | Load* |
| MMP-8 | 0.89† | IL-6 | 0.82† | TNF-α | 0.84† | IL-10 | 0.87† | MMP-3 | 0.79† |
| MMP-9 | 0.88† | IL-1β | 0.70† | IL-1β | 0.40 | IL-6 | 0.27 | IL-6 | 0.34 |
| IL-8 | 0.49 | IL-8 | 0.63† | IL-8 | 0.35 | TNF-α | 0.26 | MMP-9 | 0.24 |
| IL-1β | 0.44 | TNF-α | 0.35 | IL-10 | 0.24 | IL-8 | 0.26 | MMP-8 | 0.19 |
| MMP-3 | 0.39 | MMP-3 | 0.33 | MMP-3 | 0.21 | MMP-3 | 0.22 | IL-10 | 0.19 |
| IL-10 | 0.25 | IL-10 | 0.28 | IL-6 | 0.19 | MMP-9 | 0.20 | TNF-α | 0.19 |
| TNF-α | 0.23 | MMP-8 | 0.26 | MMP-8 | 0.19 | MMP-8 | 0.17 | IL-8 | 0.15 |
| IL-6 | 0.16 | MMP-9 | 0.22 | MMP-9 | 0.15 | IL-1β | 0.15 | IL-1β | 0.11 |

*Factor loads are determined by the pearson correlation coefficient of the marker on the component
†Factor loads >0.6 were considered for the interpretation of the component

Example 3

Multiple Linear and Logistic Regression Model of PCA Components

Table 3 presents the results of the multiple linear regression model of the PCA components on $HbA_{1c}$, adjusted for age, sex, race, BMI, duration of diabetes, and gingival condition. In this model, a significant linear association was found between PCA component 1 (MMP-8 and MMP-9 loaded highly) and PCA component 3 (TNF-α loaded highly) with $HbA_{1c}$ (0 0.28±0.14, p=0.045; (3 0.31±0.14, p=0.029; respectively). The other PCA components were not found to be linearly associated with $HbA_{1c}$ (p>0.05).

TABLE 3

Multiple* linear regression of PCA components on HbA1c

| Marker | β ± SE | p-value |
|---|---|---|
| PCA Component 1 (MMP-8 & MMP-9) | 0.28 ± 0.14 | 0.045 |
| PCA Component 2 (IL-6, IL-1β, & IL-8) | −0.02 ± 0.14 | 0.901 |
| PCA Component 3 (TNF-α) | 0.31 ± 0.14 | 0.029 |
| PCA Component 4 (IL-10) | −0.11 ± 0.14 | 0.421 |
| PCA Component 5 (MMP-3) | 0.21 ± 0.14 | 0.123 |

*Adjusted for age, duration, BMI, sex, and gingival condition

Table 4 summarizes the results of the multiple logistic regression model of the PCA components on the self-reported gingival condition. PCA component 2 (in which IL-6, IL-1β, and IL-8 loaded highly) was significantly associated with poorer gingival condition (OR 1.60, 95% CI 1.09-2.34; p-value 0.016) after adjustment for age, duration of diabetes, $HbA_{1c}$, BMI, and sex. This result suggests that high values for these markers are associated with decreased gingival condition. None of the other PCA components was significantly associated with gingival condition (p>0.05).

TABLE 4

Multiple* logistic regression of PCA components on condition of gums (poor + fair + good vs. very good + excellent)

| Marker | OR (95% CI) | p-value |
|---|---|---|
| PCA Component 1 (MMP-8 & MMP-9) | 1.16 (0.79, 1.70) | 0.463 |
| PCA Component 2 (IL-6, IL-1β, & IL-8) | 1.60 (1.09, 2.34) | 0.016 |
| PCA Component 3 (TNF-α) | 0.75 (0.52, 1.10) | 0.141 |
| PCA Component 4 (IL-10) | 1.07 (0.74, 1.54) | 0.717 |
| PCA Component 5 (MMP-3) | 1.05 (0.72, 1.53) | 0.798 |

*Adjusted for age, duration of diabetes, HbA1c, BMI, sex

The present invention provides the initial biomarker variables utilized for salivary diagnostic purposes to establish predictive models for both periodontal status and glycemic control. Taken together, enhanced T1D salivary diagnostics increases the therapeutic window for clinical intervention of both periodontitis and T1D management and eventual prediction.

The present invention demonstrates that specific salivary inflammatory markers in T1D subjects are associated with decreased glycemic control. Two principal components are associated with decreased glycemic control. The inflammatory markers that loaded strongly on these components are MMP-8, MMP-9, and TNF-α. This is the first time the association of multiple salivary inflammatory biomarkers with glycemic control and self-reported gingival condition in T1D subjects has been reported.

Prior studies examining salivary inflammatory levels within general systemic diseases, T1D, and type 2 diabetes (T2D) have demonstrated that specific mediators of inflammation are elevated within the saliva of these respective cohorts. A large study examining the salivary concentrations of 1000 adults in southern Sweden for levels of IL-1β, -6, -8, TNF-α, and MMP-8 (similar to inflammatory markers examined in this study) measured increased levels of: (1) IL-8 in subjects with tumor and bowel diseases, (2) MMP-8 in those following cardiac surgery or with diabetes and muscle diseases and (3) IL-1β, -8, and MMP-8 in those having muscle or joint diseases (Rathnayake et al., 2013). With regard to salivary inflammatory burden in T1D, Dakovic et al., 2013, examined IL-8 salivary levels in T1D subjects with or without concomitant periodontitis versus the non-T1D cohort (n=20 per group). Measured levels of IL-8 were significantly elevated in T1D subjects as compared to the non-T1D group. Within the T1D cohort, IL-8 levels were not associated with either periodontitis or clinical parameters. In respect to T2D, Yoon et al., 2012, examined unstimulated saliva samples in 192 subjects with or without T2D and revealed that IL-1β concentration in saliva was mainly associated with the degree of periodontal disease not diabetes. Another investigation demonstrated that poor glycemic control (HbA1c>8) was significantly associated with increased IL-1β levels in gingival crevicular fluid in T2D (Engebretson et al., 2004). In a later report, IL-8 levels did not associate with increased HbA1c (Engebretson et al., 2006). Taken together, these findings solidify the central hypothesis that salivary inflammatory burden can be associated with diseases of autoimmunity, metabolic control and periodontitis.

Proteomic and peptidomic analysis has revealed significant differences in the saliva between those subjects with T1D and periodontitis versus those with T1D and without periodontitis (Caseiro et al., 2013; Cabras et al., 2010;

Caseiro et al., 2012). Concordantly, a recent study evaluating 153 subjects with T1D or T2D examined the proteomic profile of these individuals stratified by their HbA1c levels ranging from <7 to >10 (Bencharit et al., 2013). PCA and cluster analysis revealed that salivary proteomic changes were associated with HbA1c sub-groupings and to some extent supported our findings in that systemic glycemic levels are reflected within the salivary milieu in an HbA1c dependent manner. Their findings revealed that salivary proteomes are distinctly segregated when compared with low (HbA1c<7), medium (8-9), and high (>10) HbA1c levels. The proteomic changes based on HbA1c were stronger in T1D rather than T2D subjects and the identified salivary proteins associated with HbA1c changes in individual samples included albumin, hemoglobin, alpha-2-macroglobin, serum amyloid A, sereotransferrin, and numerous others. Interestingly, neither cytokines nor MMP's were identified within the salivary proteome as associated with HbA1c within T1D. There was no mention of periodontal status within this study. Nonetheless, their findings in combination with the present invention clearly demonstrate that glycemic levels as reflected by HbA1c can be associated and represented in the saliva as measured by various biomarkers that can originate from the salivary gland, serum, or host immune system.

A recent report by Engebretson et al., 2013, revealed that periodontal intervention (nonsurgical) failed to promote glycemic control in T2D subjects displaying moderate to advanced chronic periodontitis. These findings would be somewhat discordant with the present invention, indicating that increased inflammatory burden is association with decreased glycemic control. However, systematic reviews and meta-analysis of numerous studies examining this relationship have indicated that periodontal treatment can result in modest reduction of HbA1c in combination with improvement of periodontal status in T2D subjects (Wang et al., 2014; Teeuw et al., 2010; Sgolastra et al., 2013; Engebretson and Kocher, 2013). This type of comprehensive analysis has yet to be as extensively examined in T1D subjects with varied periodontal status as this was the primary cohort of the present invention. Nonetheless, the present invention is certainly consistent with the overall theme that oral inflammatory levels are associated with glycemic control and potentially autoimmunity in T1D.

One of the primary goals of the present invention was to measure and determine the association of salivary inflammation with glycemic control within T1D. Since glycemic control is an important component of T1D clinical management, but not for those without diabetes, it was determined that this population was particularly relevant for the study leading to this invention. Previous literature has examined the gross comparison of salivary inflammation between diabetic (T1D and T2D) and non-diabetic controls and therefore, it was not intended to repeat these examinations (Yoon et al., 2012; Dakovic et al., 2013). While a comparison with non-diabetic controls is not provided, it is demonstrated that salivary inflammatory markers are significantly associated with increasing HbA1c in a linear model, after adjustment for potential confounders.

Another objective of the present invention is to measure and examine quantitative measures of salivary inflammation with glycemic status in a T1D cohort. Clinical measures of periodontitis and periodontal inflammation obtained from an examination is strictly a qualitative determination of the inflammatory response. This is accounted for via self-reported gingival condition. Measurement of inflammatory mediators in the saliva provides a more comprehensive analysis of oral inflammation (Kaufman and Lamster, 2002). In addition, the inflammatory mediators utilized within this invention that had the greatest association with increased HbA1c levels (TNF-$\alpha$, MMP8 and MMP9) have all been previously documented to be increased and associated with decreased periodontal status (Miller et al., 2006; Miller et al., 2010; Gursoy et al., 2013).

Salivary diagnostics have tremendous translational potential for numerous biological and technical reasons. The outstanding utility of the saliva for serving as a clinical focal point during routine dental examinations or physician visits and potentially enabling large investigational studies certainly warrants this effort. As compared to blood collection, salivary evaluation is relatively easy to obtain with high patient compliance (in the present study only 1% of subjects declined participation) and can be performed by minimally trained personnel with little post-collection processing. The present invention suggests that the salivary inflammatory burden may also be an indication of glycemic status or clinical management in T1D. These data can be further utilized to establish novel clinical diagnostic tools to promote patient compliance and enhance subsequent clinical application of interventional therapy. In addition, oral inflammatory burden with biomarkers described in this invention may also be combined with other biomarkers (ie. autoantibodies in the case of T1D) either circulating or from the saliva that can be implemented to generate predictive models to identify subjects in the early stages of either developing autoimmunity or glucose intolerance.

REFERENCES

Demmer R T, Papapanou P N. Epidemiologic patterns of chronic and aggressive periodontitis. Periodontol 2000 2010; 53:28-44. Cobb C M, Williams K B, Gerkovitch M M. Is the prevalence of periodontitis in the USA in decline? Periodontol 2000 2009; 50:13-24.

Offenbacher S, Beck J D, Moss K. Results From the Periodontitis and Vascular Events (PAVE) Study: A Pilot Multicentered, Randomized, Controlled Trial to Study Effects of Periodontal Therapy in a Secondary Prevention Model of Cardiovascular Disease. J Periodontol 2009; 80:190-201.

Noble J M, Borrell L N, Papapanou P N, Elkind M S, Scarmeas N, Wright C B. Periodontitis is associated with cognitive impairment among older adults: analysis of NHANES-III. J Neurol Neurosurg Psychiatry 2009; 80:1206-11.

Mealey B L, Rose L F. Diabetes mellitus and inflammatory periodontal diseases. Curr Opin Endocrinol Diabetes Obes 2008; 15:135-41.

Mealey B L, Oates T W. Diabetes mellitus and periodontal diseases. J Periodontol 2006; 77:1289-303.

Lalla E, Cheng B, Lal S. Periodontal changes in children and adolescents with diabetes: a casecontrol study. Diabetes Care 2006; 29:295-9.

Mealey B L. Periodontal disease and diabetes. A two-way street. J Am Dent Assoc 2006; 137 Suppl:26S-31S.

Campus G, Salem A, Uzzau S, Baldoni E, Tonolo G. Diabetes and periodontal disease: a case-control study. J Periodontol 2005; 76:418-25.

Tsai C, Hayes C, Taylor G W. Glycemic control of type 2 diabetes and severe periodontal disease in the US adult population. Community Dent Oral Epidemiol 2002; 30:182-92.

Liese A D, Lawson A, Song H R. Evaluating geographic variation in Type 1 and type 2 diabetes mellitus incidence in youth in four US regions. Health Place 2010; 16:547-56.

Atkinson M A, Maclaren N K. The pathogenesis of insulin-dependent diabetes mellitus. N Engl J Med 1994; 331:1428-36.

Mealey B. Diabetes and periodontal diseases. J Periodontol 1999; 70:935-49.

Nathan D M, Lachin J, Cleary P. Intensive diabetes therapy and carotid intima-media thickness in Type 1 diabetes mellitus. N Engl J Med 2003; 348:2294-303.

Kilpatrick E S, Keevil B G, Jagger C, Spooner R J, Small M. Determinants of raised C-reactive protein concentration in Type 1 diabetes. QJM 2000; 93:231-6.

King D E, Mainous A G, 3rd, Buchanan T A, Pearson W S. C-reactive protein and glycemic control in adults with diabetes. Diabetes Care 2003; 26:1535-9.

Schram M T, Chaturvedi N, Schalkwijk C G, Fuller J H, Stehouwer C D, Group EPCS. Markers of inflammation are cross-sectionally associated with microvascular complications and cardiovascular disease in Type 1 diabetes—the EURODIAB Prospective Complications Study. Diabetologia 2005; 48:370-8.

Chiappin S, Antonelli G, Gatti R, De Palo E F. Saliva specimen: a new laboratory tool for diagnostic and basic investigation. Clin Chim Acta 2007; 383:30-40.

Lima D P, Diniz D G, Moimaz S A, Sumida D H, Okamoto A C. Saliva: reflection of the body. Int J Infect Dis 2010; 14:e184-8.

Giannobile W V, Beikler T, Kinney J S, Ramseier C A, Morelli T, Wong D T. Saliva as a diagnostic tool for periodontal disease: current state and future directions. Periodontol 2000 2009; 50:52-64.

Gursoy U K, Könönen E, Uitto V-J. Salivary interleukin-1βconcentration and the presence of multiple pathogens in periodontitis. J Clin Periodontol 2009; 36:922-7.

Gursoy U K, Kononen E, Pradhan-Palikhe P. Salivary MMP-8, TIMP-1, and ICTP as markers of advanced periodontitis. J Clin Periodontol 2010; 37:487-93.

Eke P I, Thornton-Evans G O, Wei L, Borgnakke W S, Dye B A. Accuracy of NHANES periodontal examination protocols. J Dent Res 2010; 89:1208-13.

Darveau R P. Periodontitis: a polymicrobial disruption of host homeostasis. Nat Rev Microbiol 2010; 8:481-90.

Garlet G P. Destructive and protective roles of cytokines in periodontitis: a re-appraisal from host defense and tissue destruction viewpoints. J Dent Res 2010; 89:1349-63.

Smit M D, Westra J, Vissink A, Doornbos-van der Meer B, Brouwer E, van Winkelhoff A J. Periodontitis in established rheumatoid arthritis patients: a cross-sectional clinical, microbiological and serological study. Arthritis Res Ther 2012; 14:R222.

Dietrich T, Sharma P, Walter C, Weston P, Beck J. The epidemiological evidence behind the association between periodontitis and incident atherosclerotic cardiovascular disease. J Periodontol 2013; 84:570-84.

Kim H D, Sim S J, Moon J Y, Hong Y C, Han D H. Association between periodontitis and hemorrhagic stroke among Koreans: a case-control study. J Periodontol 2010; 81:658-65.

Mealey B L, Ocampo G L. Diabetes mellitus and periodontal disease. Periodontol 2000 2007; 44:127-53.

Atkinson M A, Eisenbarth G S. Type 1 diabetes: new perspectives on disease pathogenesis and treatment. Lancet 2001; 358:221-9.

Imperatore G, Boyle J P, Thompson T J. Projections of Type 1 and type 2 diabetes burden in the U.S. population aged <20 years through 2050: dynamic modeling of incidence, mortality, and population growth. Diabetes Care 2012; 35:2515-20.

Miller L S, Manwell M A, Newbold D. The relationship between reduction in periodontal inflammation and diabetes control: a report of 9 cases. J Periodontol 1992; 63:843-8.

Grossi S G, Skrepcinski F B, DeCaro T, Zambon J J, Cummins D, Genco R J. Response to periodontal therapy in diabetics and smokers. J Periodontol 1996; 67:1094-102.

Grossi S G, Skrepcinski F B, DeCaro T. Treatment of periodontal disease in diabetics reduces glycated hemoglobin. J Periodontol 1997; 68:713-9.

Kiran M, Arpak N, Unsal E, Erdogan M F. The effect of improved periodontal health on metabolic control in type 2 diabetes mellitus. J Clin Periodontol 2005; 32:266-72.

Papapanou P N, Sedaghatfar M H, Demmer R T. Periodontal therapy alters gene expression of peripheral blood monocytes. J Clin Periodontol 2007; 34:736-47.

Ziegler R, Heidtmann B, Hilgard D, Hofer S, Rosenbauer J, Holl R. Frequency of SMBG correlates with HbA1c and acute complications in children and adolescents with Type 1 diabetes. Pediatr Diabetes 2011; 12:11-7.

Franciosi M, Pellegrini F, De Berardis G. The impact of blood glucose self-monitoring on metabolic control and quality of life in type 2 diabetic patients: an urgent need for better educational strategies. Diabetes Care 2001; 24:1870-7.

Franciosi M, Pellegrini F, De Berardis G. Self-monitoring of blood glucose in non-insulin-treated diabetic patients: a longitudinal evaluation of its impact on metabolic control. Diabet Med 2005; 22:900-6.

Rosilio M, Cotton J B, Wieliczko M C. Factors associated with glycemic control. A cross-sectional nationwide study in 2,579 French children with Type 1 diabetes. The French Pediatric Diabetes Group. Diabetes Care 1998; 21:1146-53.

Simmons J H, McFann K K, Brown A C. Reliability of the Diabetes Fear of Injecting and Self-Testing Questionnaire in pediatric patients with Type 1 diabetes. Diabetes Care 2007; 30:987-8.

Hamilton J G. Needle phobia: a neglected diagnosis. J Fam Pract 1995; 41:169-75.

Edgar W M. Saliva: its secretion, composition and functions. Br Dent J 1992; 172:305-12.

Lyu S Y, Morisky D E, Yeh C Y, Twu S J, Peng E Y, Malow R M. Acceptability of rapid oral fluid HIV testing among male injection drug users in Taiwan, 1997 and 2007. AIDS Care 2011; 23:508-14.

White B, Day C, Thein H H. Acceptability of hepatitis C virus testing methods among injecting drug users. Drug Alcohol Rev 2008; 27:666-70.

Pfaffe T, Cooper-White J, Beyerlein P, Kostner K, Punyadeera C. Diagnostic potential of saliva: current state and future applications. Clin Chem 2011; 57:675-87.

Dillon M C, Opris D C, Kopanczyk R. Detection of homocysteine and C-reactive protein in the saliva of healthy adults: comparison with blood levels. Biomark Insights 2010; 5:57-61.

Hu S, Arellano M, Boontheung P. Salivary proteomics for oral cancer biomarker discovery. Clin Cancer Res 2008; 14:6246-52.

Streckfus C, Bigler L, Dellinger T, Dai X, Kingman A, Thigpen J T. The presence of soluble c-erbB-2 in saliva and serum among women with breast carcinoma: a preliminary study. Clin Cancer Res 2000; 6:2363-70.

Caseiro A, Ferreira R, Padrao A. Salivary Proteome and Peptidome Profiling in Type 1 Diabetes Mellitus Using a Quantitative Approach. J Proteome Res 2013 [epub ahead of print].

Cabras T, Pisano E, Mastinu A. Alterations of the salivary secretory peptidome profile in children affected by Type 1 diabetes. Mol Cell Proteomics 2010; 9:2099-108.

Caseiro A, Vitorino R, Banos A S. Salivary peptidome in Type 1 diabetes mellitus. Biomed Chromatogr 2012; 26:571-82.

Loesche W J, Syed S A, Stoll J. Trypsin-like activity in subgingival plaque. A diagnostic marker for spirochetes and periodontal disease? J Periodontol 1987; 58:266-73.

Ramseier C A, Kinney J S, Herr A E. Identification of pathogen and host-response markers correlated with periodontal disease. J Periodontol 2009; 80:436-46.

Giannobile W V. Salivary diagnostics for periodontal diseases. J Am Dent Assoc 2012; 143:6S-11S.

Gilbert G H, Litaker M S. Validity of self-reported periodontal status in the Florida dental care study. J Periodontol 2007; 78:1429-38.

Rabinovitch A. Immunoregulatory and cytokine imbalances in the pathogenesis of IDDM. Therapeutic intervention by immunostimulation? Diabetes 1994; 43:613-21.

Rabinovitch A, Suarez-Pinzon W, El-Sheikh A, Sorensen O, Power R F. Cytokine gene expression in pancreatic islet-infiltrating leukocytes of B B rats: expression of Th1 cytokines correlates with beta-cell destructive insulitis and IDDM. Diabetes 1996; 45:749-54.

Green E A, Eynon E E, Flavell R A. Local expression of TNFalpha in neonatal NOD mice promotes diabetes by enhancing presentation of islet antigens. Immunity 1998; 9:733-43.

Ebersole J L, Schuster J L, Stevens J. Patterns of salivary analytes provide diagnostic capacity for distinguishing chronic adult periodontitis from health. J Clin Immunol 2013; 33:271-9.

Standards of medical care in diabetes—2012. Diabetes Care 2012; 35 Suppl 1:S11-63.

Hannas A R, Pereira J C, Granjeiro J M, Tjaderhane L. The role of matrix metalloproteinases in the oral environment. Acta Odontol Scand 2007; 65:1-13.

Silva J A, Ferrucci D L, Peroni L A. Sequential IL-23 and IL-17 and increased Mmp8 and Mmp14 expression characterize the progression of an experimental model of periodontal disease in Type 1 diabetes. J Cell Physiol 2012; 227:2441-50.

Alman A C, Kinney G L, Tracy R P. Prospective Association Between Inflammatory Markers and Progression of Coronary Artery Calcification in Adults With and Without Type 1 Diabetes. Diabetes Care 2013., [epub ahead of print]

MacKinnon D P. Introduction to statistical mediation analysis. New York: Erlbaum; 2008.

Tofighi D, MacKinnon D P. R Mediation: An R package for mediation analysis confidence intervals. Behavior Research Methods 2011; 43:692-700.

Behle J H, Sedaghatfar M H, Demmer R T. Heterogeneity of systemic inflammatory responses to periodontal therapy. J Clin Periodontol 2009; 36:287-94.

Preshaw P M, Alba A L, Herrera D, Jepsen S, Konstantinidis A, Makrilakis K, et al. Periodontitis and diabetes: a two-way relationship. Diabetologia. 2012; 55(1):21-31.

Atkinson M A, Eisenbarth G S, Michels A W. Type 1 diabetes. Lancet. 2014; 383(9911):69-82.

Ajita M, Karan P, Vivek G, S M A, Anuj M. Periodontal disease and Type 1 diabetes mellitus: associations with glycemic control and complications: an Indian perspective. Diabetes Metab Syndr. 2013; 7(2):61-3.

Yoon A J, Cheng B, Philipone E, Turner R, Lamster I B. Inflammatory biomarkers in saliva: assessing the strength of association of diabetes mellitus and periodontal status with the oral inflammatory burden. J Clin Periodontol. 2012; 39(5):434-40.

Kaufman E, Lamster I B. The diagnostic applications of saliva—A review. Crit Rev Oral Biol M. 2002; 13(2):197-212.

Caseiro A, Ferreira R, Padrao A, Quintaneiro C, Pereira A, Marinheiro R, et al. Salivary Proteome and Peptidome Profiling in Type 1 Diabetes Mellitus Using a Quantitative Approach. J Proteome Res. 2013; 12(4):1700-9.

Gursoy U K, Kononen E, Pussinen P J, Tervahartiala T, Hyvarinen K, Suominen A L, et al. Use of host- and bacteria-derived salivary markers in detection of periodontitis: A cumulative approach. Dis Markers. 2011; 30(6):299-305.

Rathnayake N, Akerman S, Klinge B, Lundegren N, Jansson H, Tryselius Y, et al. Salivary biomarkers for detection of systemic diseases. PLoS One. 2013; 8(4):e61356.

Miller C S, King C P, Jr., Langub M C, Kryscio R J, Thomas M V. Salivary biomarkers of existing periodontal disease: a cross-sectional study. J Am Dent Assoc. 2006; 137(3):322-9.

Binnie V, McHugh S, Macpherson L, Borland B, Moir K, Malik K. The validation of self-reported smoking status by analysing cotinine levels in stimulated and unstimulated saliva, serum and urine. Oral Dis. 2004; 10(5):287-93.

Etter J F, Vu Duc T, Perneger T V. Saliva cotinine levels in smokers and nonsmokers. Am J Epidemiol. 2000; 151(3):251-8.

Dakovic D, Colic M, Cakic S, Mileusnic I, Hajdukovic Z, Stamatovic N. Salivary interleukin-8 levels in children suffering from Type 1 diabetes mellitus. J Clin Pediatr Dent. 2013; 37(4):377-80.

Engebretson S P, Hey-Hadavi J, Ehrhardt F J, Hsu D, Celenti R S, Grbic J T, et al. Gingival crevicular fluid levels of interleukin-1beta and glycemic control in patients with chronic periodontitis and type 2 diabetes. J Periodontol. 2004; 75(9):1203-8.

Engebretson S P, Vossughi F, Hey-Hadavi J, Emingil G, Grbic J T. The influence of diabetes on gingival crevicular fluid beta-glucuronidase and interleukin-8 J Clin Periodontol. 2006; 33(11):784-90.

Engebretson S P, Hyman L G, Michalowicz B S, Schoenfeld E R, Gelato M C, Hou W, et al. The effect of nonsurgical periodontal therapy on hemoglobin A1c levels in persons with type 2 diabetes and chronic periodontitis: a randomized clinical trial. JAMA. 2013; 310(23):2523-32.

Bencharit S, Baxter S S, Carlson J, Byrd W C, Mayo M V, Border M B, et al. Salivary proteins associated with hyperglycemia in diabetes: a proteomic analysis. Mol Biosyst. 2013; 9(11):2785-97.

Wang X X, Han X, Guo X J, Luo X L, Wang D L. The Effect of Periodontal Treatment on Hemoglobin A1c Levels of Diabetic Patients: A Systematic Review and Meta-Analysis. Plos One. 2014; 9(9).

Teeuw W J, Gerdes V E A, Loos B G. Effect of Periodontal Treatment on Glycemic Control of Diabetic Patients—A systematic review and meta-analysis. Diabetes care. 2010; 33(2):421-7.

Sgolastra F, Severino M, Pietropaoli D, Gatto R, Monaco A. Effectiveness of Periodontal Treatment to Improve Metabolic Control in Patients With Chronic Periodontitis and Type 2 Diabetes: A Meta-Analysis of Randomized Clinical Trials. J Periodontol. 2013; 84(7):958-73.

Engebretson S, Kocher T. Evidence that periodontal treatment improves diabetes outcomes: a systematic review and meta-analysis. J Clin Periodontol. 2013; 40:S153-S63.

Miller C S, Foley J D, Bailey A L, Campell C L, Humphries R L, Christodoulides N, et al. Current developments in salivary diagnostics. Biomark Med. 2010; 4(1):171-89.

Gursoy U K, Kononen E, Huumonen S, Tervahartiala T, Pussinen P J, Suominen A L, et al. Salivary type I collagen degradation end-products and related matrix metalloproteinases in periodontitis. Journal of Clinical Periodontology. 2013; 40(1):18-25

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein are incorporated by reference in their entirety, including all tables, to the extent they are not inconsistent with the explicit teachings of this specification.

The invention claimed is:

1. A method for determining the levels of a set of biomarkers consisting of TNF-α, IL-1β, MMP-8, and MMP-9 in a saliva sample of a subject having Type I diabetes, the method comprising the steps of:
    a) obtaining the saliva sample from the subject,
    b) contacting the saliva sample with binding partners that specifically bind to TNF-α, IL-1β, MMP-8, and MMP-9 to form complexes between the binding partners and TNF-α, IL-1β, MMP-8, and MMP-9,
    c) detecting the formation of the complexes using a system generating quantifiable signals, and
    d) determining the levels of each biomarker from the set of biomarkers based on the quantifiable signals.

2. The method of claim 1, wherein the binding partner is an antibody or an aptamer.

3. The method of claim 1, wherein the levels of TNF-α, IL-1β, MMP-8, and MMP-9 in the saliva sample are determined by ELISA, Western blot, immunoprecipitation, immunofluorescence, radioimmunoassay, immunocytochemistry, ELISpot assay, Northern blot, multiplexed bead immunoassay, or any combination thereof.

* * * * *

UNITED STATES PATENT AND TRADEMARK OFFICE
CERTIFICATE OF CORRECTION

PATENT NO. : 9,753,041 B2
APPLICATION NO. : 14/692548
DATED : September 5, 2017
INVENTOR(S) : Amy Christine Alman and Brant Roger Burkhardt Page 1 of 1

It is certified that error appears in the above-identified patent and that said Letters Patent is hereby corrected as shown below:

On the Title Page

Item (73), "Assignee: UNIVERISTY OF SOUTH FLORIDA" should read --Assignee: UNIVERSITY OF SOUTH FLORIDA--.

In the Specification

Column 10,
Line 21, "patent)." should read --patent pending).--.

Column 13,
Line 29, "(0 0.28±0.14, p=0.045; (3 0.31±0.14," should read --(β 0.28 ± 0.14, p=0.045; β 0.31±0.14,--.

Signed and Sealed this
Twenty-sixth Day of June, 2018

Andrei Iancu
*Director of the United States Patent and Trademark Office*